United States Patent [19]

van Venrooy

[11] 4,012,400
[45] Mar. 15, 1977

[54] PREPARATION OF SULFONATES FROM SULTONES

[75] Inventor: John J. van Venrooy, Media, Pa.

[73] Assignee: Sun Ventures, Inc., St. Davids, Pa.

[22] Filed: Apr. 22, 1975

[21] Appl. No.: 570,931

[52] U.S. Cl. .................. 260/448 R; 260/513 R
[51] Int. Cl.² .......................... C07F 5/06
[58] Field of Search .................. 260/448 R, 513 R

[56] References Cited

UNITED STATES PATENTS

| | | | |
|---|---|---|---|
| 3,311,650 | 3/1967 | Johnson | 260/448 R |
| 3,341,561 | 9/1967 | Starks | 260/448 R |
| 3,463,809 | 8/1969 | Crocker | 260/448 R X |
| 3,883,583 | 5/1975 | Nagayama et al. | 260/513 R |
| 3,888,918 | 6/1975 | Kuchnhauss | 260/513 R |

Primary Examiner—Helen M. S. Sneed
Attorney, Agent, or Firm—J. Edward Hess; Donald R. Johnson; Paul Lipsitz

[57] ABSTRACT

A process for the preparation of aluminum trialkyl sulfonates which are useful as intermediates to alkyl sulfonate surfactants which comprises reacting a long chain trialkyl aluminum at a temperature between about 100° C. and about 250° C. with a sultone of structure

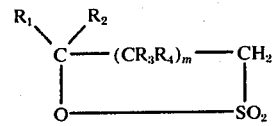

where $R_1$, $R_2$, $R_3$ and $R_4$ are hydrogen or lower alkyl and m is an integer from 1 to 2.

8 Claims, No Drawings

PREPARATION OF SULFONATES FROM SULTONES

It is known in the art to produce surfactant composition by reaction of an organo aluminum compound such as trihexyl- or tricotyl aluminum with a sulfonating agent such as $SO_3$ to obtain the aluminum sulfonate complex which is converted to a surfactant (see U.S. Pat. No. 3,311,650). The higher trialkyl aluminum may be obtained by the well known Ziegler method of adding ethylene to a lower trialkyl aluminum. It is also known that sultones, made from a long chain α-olefin and $SO_3$, may by hydrolyzed to surfactant composition (Journal of the Japan Oil Chemists Society, 19 359, 1970). However, the products of the hydrolysis reaction yields a mixture of hydroxy sulfonates and alkenesulfonates, and the hydroxysulfonates are undesirable because of their poor detergency characteristics.

The presence of impurities while of little importance in some applications is particularly detrimental to those surfactants used for more demanding applications such as the tertiary recovery of oil from oil fields and the separation of hydrocarbon values from tar sands and shales. Such surfactants must not only have high detergent activity and be of high purity but must also be thermally stable to hydrolysis and be tolerant of multivalent cations.

The process of this invention provides a novel process for making aluminum sulfonates of the formula $Al(OSO_2C_nH_{2n+1})_3$ where n is an integer of from about 10 to about 22. In accord with the invention, a long chain aluminum alkyl compound: e.g., a compound of the formula $Al(C_nH_{2n+1})_3$ wherein $n$ is an integer of from about 10 to about 22 is reacted at a temperature of from about 100° C. to about 250° C. with a sultone of the formula

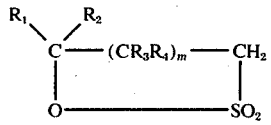

where $m$ is an integer from 1 to 2. The aluminum alkyl compound thus formed may be hydrolyzed readily by reaction with caustic (e.g., an alkali metal hydroxide such as NaOH) to yield surfactant in high purity. Another embodiment of the invention is the preparation of surfactants by hydrolysis of the aluminum trialkyl sulfonates.

The sultones useful in the invention are defined above as the five and six numbered ring sultones and will include 1,3-propane sultone, 1,4-butane sultone, 2,3,3-trimethyl-1,3-propane sultone, 2,3-dimethyl-3 ethyl-1,3-propane sultone and the like. The alkyl portion of the sultone ring may be singly or multiply substituted with lower alkyl groups known to be inert in the presence of aluminum alkyls. These sultones and their preparation from $SO_3$ and the appropriate olefin are known in the art.

In carryng out the process of the invention the aluminum alkyl compound and the sultone are simply mixed and heated with good agiation in an inert atmosphere (due to the reactivity of the aluminum alkyl) at a temperature of from about 100° C. to about 250° C. The temperature range chosen depends on the reactivity of the particular sultone being used and the reaction time. Time may be exchanged for temperature but only within the limits of the thermal stability of the reagents, particularly the sultone which may discolor when overheated, and for this reason temperatures in the range of from about 150° C. to about 200° C. are preferred. Conditions of localized overheating should be avoided by insuring vigorous mixing. The reaction product generally has the appearance of a water-white gel and is best handled simply by immediate reaction with water in the presence of alkali to convert it directly to the corresponding surfactant; e.g., compound of the formula $C_nH_{2n+1}SO_3Na$ where $n$ is defined above. Such compounds are of particular value as detergents in secondary recovery of oil from partially depleted wells because of their high detergency and hydrolytic stability at elevated temperatures.

It is known that aluminum soaps effect gellation of hydrocarbons and the products of the process of this invention are also useful for this purpose. In a preferred technique for obtaining such gelled hydrocarbons, the dry hydrocarbon is simply added to the reactants and gelling of the mass occurs upon completion of the reaction.

In order to illustrate the invention further the following examples are given.

EXAMPLE 1

To a heavy walled 75 ml. glass tube was charged 5.2 gms. of aluminum tri-n-decyl, $Al(C_{10}H_{21})_3$ having an assay of 87% active ingredient. To this was added 3.66 gms. of 1,3-sultone, $C_3H_6O_3S$. The glass tube had previously been oven dried and filled with dried nitrogen. All material transfers were handled in an inert atmosphere. The glass tube was fitted with a septum to permit sampling during the course of the experiment and contained a teflon coated mixing bar. The tube was immersed in an oil heating bath and was vibrated by means of a laboratory wrist shaker. The reaction mixture was heated to 100°–110° C. for four hours. Infrared and NMR analysis revealed that significant reaction had not occured, i.e., greater than about 10% since these methods are not sensitive to small amounts of materials. Increasing the temperature to 130° C.–150° C. for 2 additional hours failed to show any significant amount of reaction. At this point the cooled reaction mixture consisted of two water-white liquid layers, the still uncrystallized propane sultone being on the bottom. The reaction mixture was then heated to 175°–185° C. for 6 hours. On cooling to room temperature a water-white very gelatinous product was obtained and IR and NMR analysis revealed that substantial reaction had occurred. The reaction product was dumped into water and stirred vigorously while adding NaOH until the resulting solution reached a pH of 12. The water was evaporatd away leaving a white soapy solid material which was further dried in a cool vacuum oven. The reaction product was analyzed for surfactant content by titration with cetylpyidinium bromide and methylene blue as described in "Identification and Analysis of Surface - Active Agents", by Dieter Hummel, Interscience, N.Y. 1962. The reaction product was found to contain 34 wt. % anionic detergent on a water-free basis. The reaction product contains $Al(OH)_3$ which is removed by simple filtration from an aqueous or methanolic solution.

EXAMPLE 2

A three neck flask was charged with 15.9 gms of aluminum tri-n-decyl, 12.9 gms. of 1,3-propane sultone and 18.1 gms. of tetralin. The tetralin had previously been dried over molecular sieves. The flask was equipped with an efficient stirrer, a water cooled condenser, a thermometer and a gas inlet tube. A very slow purge of pre-purified nitrogen was passed through the reactor at all times. The reaction mixture was heated rapidly to 175° C. for 10 hours. Upon cooling to room temperature the flask was filled with a clear gel. This shows the ability of the reaction product, an aluminum soap, to be formed in the presence of a suitable hydrocarbon and to gel the entire system.

The aluminum soap-tetraline gel was dumped into water and reacted with NaOH and the amount anionic detergent formed analyzed as described by the method used in Example 1. On a water and tetralin free basis the reaction product was found to contain 40.3 wt. % anionic detergent.

EXAMPLE 3

To a heavy walled glass tube was charged 4.0 gms. of aluminum tri-n-decyl having an assay of 87% active ingredient. To this was added 3.14 gms. of 1,4-butane sultone, $C_4H_8O_3S$. Handling procedures were as described in Example 1. The reaction mixture was heated at 105°–110° C. for 7 hours. Infra-red and NMR anaylsis did not indicate that any significant amount of reaction had occurred. The reaction mixture was then heated for an additional 7 hours at 165°–175° C. Infrared and NMR analysis revealed that a small amount of reaction had taken place, therefore the reaction mixture was heated for an additional 7 hours at 175°–180° C. On cooling the reaction product was a clear gelatinous mass. The reaction product was dumped into water and reacted with NaOH until the resulting solution was basic to litmus. The water was evaporated away leaving a white, soapy product which on analysis as described in Example 1 was found to be 20.5 wt. % anionic detergent. This shows the lower reactivity of the six membered ring sultone versus the five membered ring sultone.

EXAMPLE 4

To a three necked flask equipped as in Example 2 was charged 28.3 gms. of aluminum tri-n-decyl and 14.4 gms. of 1,3-propane sultone. The reaction mixture was heated rapidly to 210° C. for one-half hour then cooled rapidly. After the usual NaOH work-up procedure as previously described, the reaction product was found to contain 36.9 wt. % anionic detergent. It is important to maintain vigorous agitation to prevent localized overheating which may result in a discolored product particularly when operating at this high a temperature.

EXAMPLE 5

To a heavy walled glass tube was charged 4.9 gms. of aluminum tri-n-decyl having an assay of 87% active ingredients. To this was added 4.7 gms. of 2,3,3-trimethyl-1,3-propane sultone, The 2,3,3-trimethyl-1,3,-propane sultone was prepared by reacting sulfur trioxide and 3,3-dimethyl-butene-1 as described in the method of M. D. Robbins and C. D. Broaddus reported in J. Org. Chem., Vol. 39, No. 16, 1974, pages 2459–61. The reaction mixture was heated for 15 hours at 100°–110° C. After the usual NaOH work-up procedure as previously described, the reaction product was found to contain 13.7 wt. % anionic detergent. This example shows that significant reaction may be achieved at low temperature with a more reactive sultone using longer reaction times.

The invention claimed is:

1. A process for the preparation of aluminum trialkyl sulfonates which comprises reacting a long chain trialkyl aluminum at a temperature between about 100° C. and about 250° C., with a sultone of the structure:

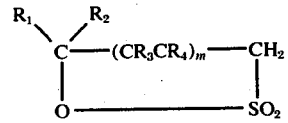

where $R_1$, $R_2$, $R_3$, and $R_4$ are hydrogen or lower alkyl and $m$ is an integer of from 1 to 2.

2. The process of claim 1 where the sultone is 1,3-propane sultone.

3. The process of claim 1 where the sultone is 1,4-butane sultone.

4. The process of claim 1 where the sultone is 2,3,3-trimethyl-1,3-propane sultone.

5. The process of claim 1 where the trialkyl aluminum is tri-n-decyl aluminum.

6. The process of claim 5 where the sultone is 1,3-propane sultone.

7. The process of claim 5 where the sultone is 1,4-butane sultone.

8. The process of claim 5 where the sultone is 2,3,3-trimethyl-1,3-propane sultone.

* * * * *